United States Patent [19]

Rivier et al.

[11] 4,215,038

[45] Jul. 29, 1980

[54] PEPTIDES WHICH INHIBIT GONADAL FUNCTION

[75] Inventors: Jean E. F. Rivier; Catherine L. Rivier; Wylie W. Vale, Jr., all of La Jolla, Calif.

[73] Assignee: The Salk Institute for Biological Studies, San Diego, Calif.

[21] Appl. No.: 950,301

[22] Filed: Oct. 16, 1978

Related U.S. Application Data

[63] Continuation-in-part of Ser. No. 855,837, Nov. 30, 1977, abandoned.

[51] Int. Cl.² .................... C07C 103/52; A61K 37/00
[52] U.S. Cl. ........................... 260/112.5 LH; 424/177
[58] Field of Search ............... 260/112.5 LH; 424/177

[56] References Cited

U.S. PATENT DOCUMENTS

| | | | |
|---|---|---|---|
| 3,928,307 | 12/1975 | Foell et al. | 260/112.5 LH |
| 3,972,859 | 8/1976 | Fujino et al. | 260/112.5 LH |
| 4,008,209 | 2/1977 | Fujino et al. | 260/112.5 LH |
| 4,010,125 | 3/1977 | Schally et al. | 260/112.5 LH |
| 4,018,726 | 4/1977 | Schally et al. | 260/112.5 LH |
| 4,034,082 | 7/1977 | Johnson et al. | 260/112.5 LH |
| 4,086,219 | 4/1978 | Wittle et al. | 260/112.5 LH |
| 4,124,703 | 11/1978 | Dutta et al. | 260/112.5 LH |

OTHER PUBLICATIONS

Rivier, et al., Peptides, 1976, 427–451.
Ling, et al., Biochem. and Biophys. Res. Commun., 63, 1975, 801–806.
Hirotsu, et al., Biochem. and Biophys. Res. Commun., 59, 1974, 277–282.

*Primary Examiner*—Delbert R. Phillips
*Attorney, Agent, or Firm*—Fitch, Even & Tabin

[57] ABSTRACT

Peptides which inhibit the secretion of gonadotropins by the pituitary gland and inhibit the release of steroids by the gonads. The peptides have the structure:

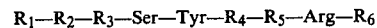

$$R_1-R_2-R_3-Ser-Tyr-R_4-R_5-Arg-R_6$$

wherein $R_1$ is selected from the group consisting of D-pGlu, D-Pro, D-Trp, D-His, D-Arg, D-Leu, Formyl D-Pro, Acetyl D-Pro, Benzoyl D-Pro and β-Ala; $R_2$ is selected from the group consisting of D-Phe, Phe, Nα Me-Phe, His, D-His, D-Trp, Trp and Nα Me-Leu; $R_3$ is selected from the group consisting of D-Trp, Trp; D-Phe, Phe, Pro and D-His; $R_4$ is selected from the group consisting of Gly, D-Trp, D-Phe and D-Tyr; $R_5$ is selected from the group consisting of Leu and Nα Me Leu; and $R_6$ is selected from the group consisting of Pro-Gly-NH₂ and Pro—NH—CH₂—CH₃.

16 Claims, No Drawings

PEPTIDES WHICH INHIBIT GONADAL FUNCTION

The invention described herein was made in the course of work under a grant or award from the Department of Health, Education and Welfare.

The present application is a Continuation-In-Part of application Ser. No. 855,837, filed Nov. 30, 1977, now abandoned.

The present invention relates to peptides which inhibit the release of gonadotropins by the pituitary gland in mammalians, including humans. More particularly, the present invention is directed to peptides which inhibit gonadal function and the release of the steroidal hormones, progesterone and testosterone.

The pituitary gland is attached by a stalk to the region in the base of the brain known as the hypothalamus. The pituitary gland has two lobes, the anterior and posterior lobes. The posterior lobe of the pituitary gland stores and passes onto the general circulation two hormones manufactured in the hypothalamus, these being vasopressin and oxytocin. The anterior lobe of the pituitary gland secretes a number of hormones, which are complex protein or glyco-protein molecules that travel through the blood stream to various organs and which, in turn, stimulate the secretion into the blood stream of other hormones from the peripheral organs. In particular, follicle stimulating hormone and luteinizing hormone, sometimes referred to as gonadotropins or gonadotropic hormones, are released by the pituitary gland. These hormones, in combination, regulate the functioning of the gonads to produce testosterone in the testes and progesterone and estrogen in the ovaries, as well as regulating the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly luteinizing hormone. For convenience, luteinizing hormone is hereinafter referred to as LH. The hypothalamic hormone which acts as a releasing factor for LH is referred to herein as LRF wherein RF stands for "releasing factor" and the L signifies that the hormone release LH. LRF has been isolated and identified.

It has been demonstrated that some female mammalians who have no ovulatory cycle and who show no pituitary or ovarian defect begin to secrete normal amounts of the gonadotropins, LH and FSH (follicle stimulating hormone) after the administration of LRF. The administration of LRF is suitable for the treatment of those cases of infertility where the functional defect resides in the hypothalamus. Ovulation can be induced in female mammalians by the administration of LRF. However, the dosage level of LRF required to influence ovulation may sometines be high. Recent reports have also indicated that the administration of large and frequent dosages of LRF actually inhibit gonadal function in female rats by disruption of the hormonal network. For this reason, LRF and analogs of LRF which are more potent than LRF to promote release of LH have been investigated for its potential use as a contraceptive. The principal disadvantage to the use of these peptides as a potential contraceptive is, of course, the requirement for large and frequent dosages. It would be desirable to provide peptides which are antagonistic to endogenous LRF and which prevent secretion of LH.

Accordingly, it is a principal object of the present invention to provide peptides which inhibit the release of gonadotropins in mammalians, including humans. Another object of the present invention is to provide peptides which inhibit the release of steroids by the gonads of male and female mammalians, including humans. A further object of the present invention is to provide peptides which have an inhibitory effect on the reproduction processes of mammalians, including humans.

These and other objects of the present invention will become more apparent from the following detailed description.

Generally, in accordance with the present invention, peptides have been synthesized which inhibit the secretion of gonadotropins by the pituitary gland of mammalians, including humans and/or inhibit the release of steroids by the gonads. The peptides act to inhibit the release of gonadotropins.

LRF has been characterized as a decapeptide having the following structure:

p-Glu-His-Trp-Ser-Tyr-Gly-Leu-Arg-Pro-Gly-NH$_2$

Peptides are compounds which contain two or more amino acids in which the carboxyl group of one acid is linked to the amino group of the other acid. The formula for LRF, as represented above, is in accordance with conventional representation of peptides where the amino group appears to the left and the carboxyl group to the right. The position of the amino groups is identified by numbering the amino groups from left to right. In the case of LRF, the hydroxyl portion of the carboxyl group has been replaced with an amino group (NH$_2$). The abbreviations for the individual amino acid groups above are conventional and are based on the trivial name of the amino acid: where p-Glu is pyroglutamic acid, His is histidine, Trp is tryptophan, Ser is serine, Tyr is tyrosine, Gly is glycine, Leu is Leucine, Arg is arginine and Pro is proline. Except for glycine, amino acids of the peptides of the invention are of the L-configuration unless noted otherwise.

It is known that the substitution of D-amino acids for Gly in the 6-position of the LRF decapeptide provides a peptide material having from about 1 to 30 times greater potency than does LRF to effect the release of luteinizing hormone and other gonadotropins by the pituitary gland of mammalians. The releasing effect is obtained when the substituted peptide is introduced into the blood stream of a mammalian.

It is also known that substitution of various amino acids for His (or the deletion of His) at the 2-position of the LRF decapeptide produces peptide material having an inhibitory effect on the release of luteinizing hormone and other gonadotropins by the pituitary gland of mammalians. In particular, varying degrees of inhibition of the release of lutenizing hormone are obtained when His is deleted or replaced by Asp, Cys, D-Ala, des His, D-Phe and Gly. It has been further discovered that the inhibitory effect of those peptides modified at the 2-position can be greatly enhanced when a D-amino acid is substituted for Gly in the 6-position of the decapeptides. For example, the peptide: pGlu-Trp-Ser-Tyr-D-Ala-Leu-Arg-Pro-Gly-NH$_2$ is 3 times more potent as an inhibitor for the release of gonadotropins than is the same peptide where Gly is present in the 6-position rather than D-Ala.

In accordance with the present invention, peptides have been synthesized which are highly potent to inhibit release of LH. These peptides have been found to inhibit ovulation in female mammals when administered at very low levels at proestrous. The peptides are also effective to cause resorption of fertilized eggs if administered shortly after conception.

The peptides of the present invention are represented by the following formula:

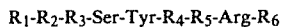

where in $R_1$ is selected from the group consisting of D-pGlu, D-Pro, D-Trp, D-His, D-Arg, D-Leu, Formyl D-Pro, Acetyl D-Pro, Benzoyl D-Pro and β-Ala, $R_2$ is selected from the group consisting of D-Phe, Phe, Nα Me-Phe, His, D-His, D-Trp, Trp and Nα Me-Leu; $R_3$ is selected from the group consisting of D-Trp, Trp; D-Phe, Phe, Pro and D-His; $R_4$ is selected from the group consisting of Gly, D-Trp, D-Phe and D-Tyr; $R_5$ is selected from the group consisting of Leu and $N^\alpha$ Me Leu and $R_6$ is selected from the group consisting of Pro-Gly-$NH_2$ and Pro-NH-$CH_2$-$CH_3$.

sized by a solid phase technique. The synthesis was conducted in a step wise manner on chloromethylated resin for those peptides wherein $R_6$ is Pro-NH-$CH_2$-$CH_3$ and on benzhydrylamine resin for those peptides wherein $R_6$ is Pro-Gly-$NH_2$. The resin was composed of fine beads (20–70 microns in diameter) of a synthetic resin prepared by copolymerization of styrene with 1 to 2% divinylbenzene. For chloromethylated resin, the benzene rings in the resin were chloromethylated in a Friedel-Crafts reaction with chloromethyl ether and stannic chloride. The chlorine thus introduced is a reactive benzyl chloride type of linkage. The Friedel-Crafts reaction is continued until the resin contains 0.5 to 2 millimoles of chlorine per gram of resin. The benzhydrylamine resin was prepared in accordance with the following:

(Step A.) FRIEDEL-CRAFTS reaction:

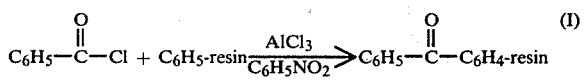

(Step B.) LEUKART'S reductive amination:

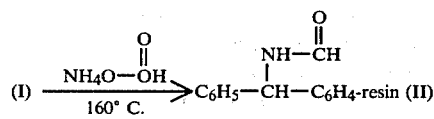

(Step C.) Hydrolysis, neutralization:

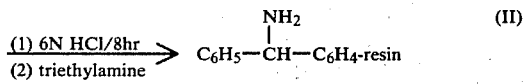

As described hereinbelow, the reagents used will be first listed by their chemical name and their common abbreviation. Thereafter, the reagent will sometimes be referred to by the common abbreviation.

In the preparation of peptides wherein $R_6$ is Pro—N-H—$CH_2$—$CH_3$, the triethylammonium salt of $N^\alpha$ Boc protected Pro is esterified onto the chloromethylated resin by refluxing in ethanol for about 48 hours. Also possible is the use of the resin or potassium salts in dimethylformamide (DMF) or dimethylsulfoxide (DMS) respectively at temperatures ranging from 40° to 80° C. After deprotection and neutralization, the $N^\alpha$ Boc derivative of the next amino acid, Arg is added along with a coupling agent which is dicyclohexylcarbodiimide (DCC). The side chain of Arg is protected with tosyl (Tos). Deprotection, neutralization and addition of successive amino acids is performed in accordance with the following schedule:

Schedule for coupling of amino acids in solid phase synthesis of D-pGlu-D-Phe-D-Trp-Ser-Tyr-D-Trp-Leu-Arg-Pro-NH-$CH_2$-$CH_3$- on 10 grams of resin.

| Step | Reagents and operations | Mix times min. |
|---|---|---|
| 1 | $CH_2Cl_2$ wash 80 ml (2 times) | 3 |
| 2 | Methanol (MeOH) wash 30 ml (2 times) | 3 |
| 3 | $CH_2Cl_2$ wash 80 ml (3 times) | 3 |
| 4 | 50 percent trifluoroacetic acid (TFA) plus 5 percent 1,2 - ethanedithiol in $CH_2Cl_2$ 70 ml (2 times) | 10 |
| 5 | $CH_2Cl_2$ wash 80 ml (2 times) | 3 |
| 6 | Triethylamine ($Et_3N$) 12.5 percent in dimethylformamide (DMF) 70 ml (2 times) | 5 |
| 7 | MeOH wash 40 ml (2 times) | 2 |
| 8 | $CH_2Cl_2$ wash 80 ml (3 time) | 3 |
| 9 | Boc-amino acid (10 mmoles) in 30 ml DMF (1 time) plus dicyclohexylcarbodiimide (DCC) (10 mmoles) in DMF | 30 |
| 10 | MeOH wash 40 ml (2 times) | 3 |
| 11 | $Et_3N$ 12.5 percent in DMF 70 ml (1 time) | 3 |
| 12 | MeOH wash 30 ml (2 times) | 3 |
| 13 | $CH_2Cl_2$ wash 80 ml (2 times) | 3 |

After step 13, an aliquot is taken for a ninhydrin test: if the test is negative, go back to step 1 for coupling of the next amino acid; if the test is positive or slightly positive, go back to steps 9 through 13.

The above schedule is used for coupling of each of the amino acids of the peptide of the invention. $N^\alpha$ Boc protection is used for each of the remaining amino acids throughout the synthesis. OBzl is used as a side chain protecting group for Ser and Tyr. 2-6 dichlorobenzyl can be used as the side chain protecting group for Tyr, p-Toluenesulfonyl (Tos), dinitrophenyl (Dnp) or Boc can be used as the side chain protecting group for His. pGlu is introduced as benzyloxycarbonyl (Z) protected amino acid.

The above method is used to provide the fully protected peptidoresin $X^1$-$R_1$-$R_2$-$R_3$-Ser($X^2$)-Tyr($X^3$)-$R_4$-$R_5$-Arg-$R_6$-O-resin in which each of the protective groups are as defined hereinbelow. If desired the fully protected peptide can be removed from the resin support by aminolysis employing dimethylamine, methylamine, ethylamine, n-propylamine, i-propylamine, butylamine, iso-butylamine, pentylamine or phenethylamine to yield the fully protected alkyl amide intermediate. For example, cleavage of the peptide from the resin is performed by stirring the resin overnight in distilled ethylamine at 0° C. in a pressure bottle. After removal of excess ethylamine by distillation under nitrogen or vacuum, the resin, suspended in methanol, is removed from the slurry by filtration. The resin is further washed successively with DMF, methanol, and a mixture of DMF and methanol. The recovered solution of cleaved, protected peptide is evaporated to dryness on a rotary vacuum evaporator at room temperature. The peptide is taken in a minimum amount of methanol to dissolve the peptide. The solution is added dropwise to a 50 times volume excess of dry ether with stirring. A flocculent precipitate appears which is recovered by filtration or centrifugation. The recovered precipitate is dried to provide the intermediates which are part of the invention.

The intermediates of the invention may be represented as:

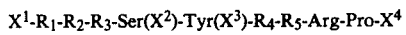

$X^1$-$R_1$-$R_2$-$R_3$-Ser($X^2$)-Tyr($X^3$)-$R_4$-$R_5$-Arg-Pro-$X^4$ where $X^1$ represents hydrogen or an α-amino protecting group; $X^2$ is a protecting group for Ser and preferably is benzyl ester (OBzl); $X^3$ is a protecting group for Tyr selected from the group consisting of OBzl and 2-6 dichlorobenzyl; and $X^4$ is selected from dimethylamine, alkylamino of 1 to 5 carbon atoms, phenethylamine, O—$CH_2$—[resin support] or Gly—O—$CH_2$—[resin support] or Gly-NH [resin support].

The criterion for selecting side chain protecting groups for $X^1$-$X^4$ are that the protecting group must be stable to the reagent under the reaction conditions selected for removing the α-amino protecting group at each step of the synthesis, the protecting group must not be split off under coupling conditions and the protecting group must be removable upon completion of the synthesis of the desired amino acid sequence under reaction conditions that will not alter the peptide chain.

The group —O—$CH_2$[resin support] or Gly—O—$CH_2$—[resin support] defining $X^4$ in the intermediates of the invention represents the ester moiety of one of the many functional groups of the polystyrene resin support. The group Gly—NH—[resin support] defining $X^4$ in the intermediates of the invention represents the amide bond of Gly to benzhydrylamine resin.

Deprotection of the peptides as well as cleavage of the peptide from the benzhydrylamine resin takes place at 0° C. with hydrofluoric acid (HF). Anisole is added to the peptide prior to treatment with HF. After the removal of HF, under vacuum, the cleaved, deprotected peptide is treated with ether, decanted, taken in dilute acetic acid and lyophilized.

Purification of the peptide is effected by ion exchange chromatography on a CMC column, followed by partition chromotography using the elution system: n-butanol; acetic acid; water (4:1:5; volume ratio). The partition chromatography column packing is Sephadex G 25.

The preparation of those peptides wherein $R_5$ is Pro-Gly-$NH_2$ on benzhydrylamine resin was in accordance with the following; $N^α$ and side chain protecting groups were the same as defined above during the synthesis:

Coupling of a residue was carried out for 1 to 5 hours in methylenechloride, dimethylformamide (DMF) or mixtures thereof using a 3-5 fold excess of BOC protected amino acids and dicyclohexylcarbodiimide (DCC) activating reagent. The first residue is attached to the benzhydrylamine resin by an amide bond. The coupling reaction throughout the synthesis was monitored by a ninhydrin test, as reported by Kaiser et al. *Anal. Biochemi.* 34 (1970) 595.

The deblocking procedure consisted of a 20 minutes treatment in TFA containing 5 percent, 1,2-ethanedithiol, followed by neutralization with triethylamine ($Et_3N$) in DMF or methylene chloride. Numerous washes with MeOH and $CH_2Cl_2$ follwed each step.

The cleavage of the peptide from the resin and complete deprotection of the peptide takes place very readily at 0° C. with hydrofluoric acid (HF). Anisol was added to the resin prior to treatment with HF. After the removal of HF, under vacuum, the resin was treated with ether, filtered and the peptide was then eluted with acetic acid and water. The combined acetic acid-water extracts were evaporated and subjected to purification.

Purification of the peptide was effected by partition chromatography in a gel filtration column using the elution system; n-Butanol; 0.1N acetic acid; (1:1; volume ratio). This was followed by a simple gel filtration using 0.5N acetic acid as eluent.

The peptides are used at a level effective to prevent ovulation of female mammalian eggs. The peptide of the invention is effective at levels of 5 milligrams per kilograms of body weight when administered at about noon on the day of proestrous to prevent ovulation. It is preferred to use dosage levels in the range of from about 0.1 to about 10 milligrams per kilograms of body weight. Higher levels can be used but no significant benefit is attained through use of higher levels.

The following examples further illustrate various features of the invention, but are intended to in no way limit the scope of the invention which is defined in the appended claims.

EXAMPLE I

The following peptides of the invention having the indicated formula were prepared by the solid phase procedure described hereinabove. For those peptides wherein $R_6$ is Pro—NH—$CH_2$—$CH_3$ a chloromethylated resin is used. A benzhydrylamine resin is used for those peptides wherein $R_6$ is Pro-Gly—$NH_2$.

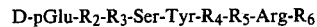

D-pGlu-$R_2$-$R_3$-Ser-Tyr-$R_4$-$R_5$-Arg-$R_6$

| Peptide Composition | $R_2$ | $R_3$ | $R_4$ | $R_5$ | $R_6$ |
|---|---|---|---|---|---|
| 1 | D-Phe | D-Trp | D-Trp | Leu | Pro—Gly—$NH_2$ |
| 2 | $N^α$ Me—Phe | D-Trp | D-Trp | Leu | Pro—Gly—$NH_2$ |
| 3 | D-Phe | D-Trp | D-Trp | $N^α$ Me—Leu | Pro—Gly—$NH_2$ |
| 4 | D-Phe | Phe | D-Trp | Leu | Pro—Gly—$NH_2$ |
| 5 | D-Phe | Pro | D-Trp | Leu | Pro—Gly—$NH_2$ |
| 6 | D-Phe | D-Trp | D-Trp | Leu | Pro—NH—$CH_2$—$CH_3$ |
| 7 | D-Phe | D-Trp | D-Trp | $N^α$ Me—Leu | Pro—NH—$CH_2$—$CH_3$ |

The peptides set forth in the foregoing table were assayed in vitro and in vivo. The in vitro assay was made using a four day old primary culture of dispersed rat pituitary cells. The levels of LH mediated in response to the application of peptides was assayed by specific radioimmunoassay for rat LH. Control dishes of cells received only $3 \times 10^{-9}$ M of LRF; experimental dishes received $3 \times 10^{-9}$ M LRF and a concentration of test peptide ranging from $10^{-9}$ M to $10^{-7}$ M. Results are expressed in Table I (In Vitro Column) are expressed as the molar ratio of test peptide required to reduce the amount of LH released by $3 \times 10^{-9}$ M LRF to 50 percent of the control value.

Thereafter, the culture was again innoculated with $3 \times 10^{-5}$ M of LRF and the molar ratio of the peptide of the invention required to suppress secretion of LH generated by the LRF was determined. This molar ratio is set forth hereinbelow in Table I.

The effectiveness of the peptide compositions of the invention was also determined in vivo, as follows: Twenty-seven day old rats were injected with 50 nanograms of LRF. Thereafter the molar ratio of the peptide required to suppress secretion of LH generated by the LRF was determined. This value is set forth hereinbelow in Table I.

TABLE I

| Peptide Composition | In Vitro<br>Molar Ratio Necessary to Produce Inhibition of LRF ($3 \times 10^{-5}$ M) Mediated LH Secretion | In Vivo<br>Molar Ratio to Suppress Secretion of LH |
|---|---|---|
| 1 | 3:1 | 50:1 |
| 2 | 30:1 | |
| 3 | 2:1 | |
| 4 | 4:1 | |
| 5 | 5:1 | |
| 6 | 3:1 | |
| 7 | 2:1 | |

Each of the peptides described hereinabove was used to determine its effectiveness to prevent ovulation in female rats. In this test, ten female rats were injected with one milligram of peptide in corn oil at about noon on the day of proestrous. Proestrous is the afternoon before estrous (ovulation). In each case, the peptide was found to be 100% effective to prevent ovulation of the female rats. A separate ten female rat group was used as a control to which the peptide was not administered. Each of the ten control rat females had ovulation at estrous.

EXAMPLE II

The following peptides of the invention having the indicated formula were prepared by the solid phase procedure described hereinabove.

$R_1$-$R_2$-$R_3$-Ser-Tyr-$R_4$-Leu-Arg-Pro-Gly-$NH_2$

| Peptide Composition | $R_1$ | $R_2$ | $R_3$ | $R_4$ |
|---|---|---|---|---|
| 8 | D-Trp | D-Phe | D-Trp | D-Trp |
| 9 | D-Arg | D-Phe | D-Trp | D-Trp |
| 10 | D-Leu | D-Phe | D-Trp | D-Trp |
| 11 | D-His | D-Phe | D-Trp | D-Trp |
| 12 | D-pGlu | D-phe | D-Trp | D-Trp |
| 13 | D-Pro | D-Phe | D-Trp | D-Trp |
| 14 | Formyl D-Pro | D-Phe | D-Trp | D-Trp |
| 15 | Acetyl D-Pro | D-Phe | D-Trp | D-Trp |
| 16 | Benzoyl D-Pro | D-Phe | D-Trp | D-Trp |
| 17 | β-Ala | D-Phe | D-Trp | D-Trp |
| 18 | D-pGlu | D-Trp | D-Trp | D-Trp |

Each of the peptides described hereinabove was used to determine its effectiveness to prevent ovulation in female rats. In this test, ten female rats having an average weight of 2 kilograms were injected with the level of the peptide indicated hereinbelow in Table II. The peptide was injected at about noon on the day of proestrous. The effectiveness of the peptide to prevent ovulation at the indicated level of injection is indicated hereinbelow in Table II for the indicated level of use. A separate ten female rat group was used as a control to which the peptide was administered. Each of the ten control rat females had ovulation at estrous.

TABLE II

| Peptide Composition | Level of Use Micrograms | Number of Rats Having Ovulation |
|---|---|---|
| 8 | 750 | 9 |
| 9 | 750 | 5 |
| 10 | 500 | 9 |
| 11 | 750 | 3 |
| 12 | 150 | 0 |
| 13 | 100 | 4 |
| 13 | 250 | 0 |
| 14 | 500 | 4 |
| 15 | — | — |
| 16 | — | — |
| 17 | 750 | 1 |
| 18 | 500 | 4 |

What is claimed is:

1. A peptide which is effective to inhibit release of steroids by the gonadotropins of mammalians, said peptide having the formula:

$R_1$-$R_2$-$R_3$-Ser-Tyr-$R_4$-$R_5$-Arg-$R_6$ wherein $R_1$ is selected from the group consisting of D-pGlu, D-Pro, D-Trp, D-His, D-Arg, D-Leu, formyl D-Pro, acetyl D-Pro, benzoyl D-Pro and β-Ala, $R_2$ is selected from the group consisting of D-Phe, D-His and D-Trp; $R_3$ is selected from the group consisting of D-Trp, D-Phe, and D-His; $R_4$ is selected from the group consisting of D-Trp, D-Phe and D-Tyr; $R_5$ is selected from the group consisting of Leu and $N^a$ Me-Leu; and $R_6$ is selected from the group consisting of Pro—Gly—$NH_2$ and Pro—NH—$CH_2$—$CH_3$.

2. A peptide in accordance with claim 1 wherein $R_1$ is D-pGlu, $R_2$ is D-Phe, $R_3$ is D-Trp, $R_4$ is D-Trp, $R_5$ is Leu and $R_6$ is Pro—Gly—$NH_2$.

3. A peptide in accordance with claim 1 wherein $R_1$ is D-pGlu, $R_2$ is D-Phe, $R_3$ is D-Trp, $R_4$ is D-Trp, $R_5$ is $N^a$ Me-Leu and $R_6$ is Pro—Gly—$NH_2$.

4. A peptide in accordance with claim 1 wherein $R_1$ is D-pGlu, $R_2$ is D-Phe, $R_3$ is D-Trp, $R_4$ is D-Trp, $R_5$ is Leu and $R_6$ is Pro—NH—$CH_2$—$CH_3$.

5. A peptide in accordance with claim 1 wherein $R_1$ is D-pGlu, $R_2$ is D-Phe, $R_3$ is D-Trp, $R_4$ is D-Trp, $R_5$ is $N^a$ Me-Leu and $R_6$ is Pro—NH—$CH_2$—$CH_3$.

6. A peptide in accordance with claim 1 wherein $R_1$ is D-Trp, $R_2$ is D-Phe, $R_3$ is D-Trp, $R_4$ is D-Trp, $R_5$ is Leu and $R_6$ is Pro—Gly—$NH_2$.

7. A peptide in accordance with claim 1 wherein $R_1$ is D-Arg, $R_2$ is D-Phe, $R_3$ is D-Trp, $R_4$ is D-Trp, $R_5$ is Leu and $R_6$ is Pro—Gly—$NH_2$.

8. A peptide in accordance with claim 1 wherein $R_1$ is D-Leu, $R_2$ is D-Phe, $R_3$ is D-Trp, $R_4$ is D-Trp, $R_5$ is Leu and $R_6$ is Pro—Gly—$NH_2$.

9. A peptide in accordance with claim 1 wherein $R_1$ is D-His, $R_2$ is D-Phe, $R_3$ is D-Trp, $R_4$ is D-Trp, $R_5$ is Leu and $R_6$ is Pro—Gly—$NH_2$.

10. A peptide in accordance with claim 1 wherein $R_1$ is D-Pro, $R_2$ is D-Phe, $R_3$ is D-Trp, $R_4$ is D-Trp, $R_5$ is Leu and $R_6$ is Pro—Gly—$NH_2$.

11. A peptide in accordance with claim 1 wherein $R_1$ is D-pGlu, $R_2$ is D-Phe, $R_3$ is D-Phe, $R_4$ is D-Trp, $R_5$ is Leu and $R_6$ is Pro—Gly—$NH_2$.

12. A peptide in accordance with claim 1 wherein $R_1$ is formyl D-Pro, $R_2$ is D-Phe, $R_3$ is D-Trp, $R_4$ is D-Trp, $R_5$ is Leu and $R_6$ is Pro—Gly—$NH_2$.

13. A peptide in accordance with claim 1 wherein $R_1$ is acetyl D-Pro, $R_2$ is D-Phe, $R_3$ is D-Trp, $R_4$ is D-Trp, $R_5$ is Leu and $R_6$ is Pro—Gly—$NH_2$.

14. A peptide in accordance with claim 1 wherein $R_1$ is benzoyl D-Pro, $R_2$ is D-Phe, $R_3$ is D-Trp, $R_4$ is D-Trp, $R_5$ is Leu and $R_6$ is Pro—Gly—$NH_2$.

15. A peptide in accordance with claim 1 wherein $R_1$ is $\beta$-Ala, $R_2$ is D-Phe, $R_3$ is D-Trp, $R_4$ is D-Trp, $R_5$ is Leu and $R_6$ is Pro—Gly—$NH_2$.

16. A peptide in accordance with claim 1 wherein $R_1$ is D-pGlu, $R_2$ is D-Trp, $R_3$ is D-Trp, $R_4$ is D-Trp, $R_5$ is Leu and $R_6$ is Pro—Gly—$NH_2$.

* * * * *

UNITED STATES PATENT AND TRADEMARK OFFICE
CERTIFICATE OF CORRECTION

PATENT NO. : 4,215,038
DATED : July 29, 1980
INVENTOR(S) : Jean E. F. Rivier et al.

It is certified that error appears in the above-identified patent and that said Letters Patent are hereby corrected as shown below:

In the Specification:

Column 1, line 48, "release" should be --releases--.

Column 1, line 59, correct the spelling of "sometimes".

Column 3, between lines 24 & 25, insert --The peptides of the present invention were synthe- --.

Column 4, line 31 - Step 8, "time" should be --times".

Signed and Sealed this

Twenty-fourth Day of February 1981

[SEAL]

Attest:

RENE D. TEGTMEYER

Attesting Officer

Acting Commissioner of Patents and Trademarks